United States Patent [19]

Porteous

[11] Patent Number: 5,678,726
[45] Date of Patent: Oct. 21, 1997

[54] ALIQUOT PORTION MEASURING VIAL WITH OVERFILL CONTROL

[76] Inventor: Don D. Porteous, 600 E. Hueneme Rd., Oxnard, Calif. 93033

[21] Appl. No.: 501,975

[22] Filed: Jul. 3, 1995

[51] Int. Cl.⁶ .............................. B65D 1/40; B65D 25/00
[52] U.S. Cl. .................. 220/676; 220/661; 220/675; 220/DIG. 13
[58] Field of Search ............................. 220/676, 661, 220/669, 675, 604, DIG. 13; 215/380, 382, 383, 384, 385

[56] References Cited

U.S. PATENT DOCUMENTS

| | | | |
|---|---|---|---|
| 1,411,990 | 4/1922 | Corson | 215/380 |
| 4,113,129 | 9/1978 | Cambio, Jr. | 215/380 |
| 4,157,762 | 6/1979 | Robinson | 220/669 |
| 4,881,650 | 11/1989 | Bartz | 215/383 X |
| 5,435,451 | 7/1995 | Dyer | 220/675 X |

FOREIGN PATENT DOCUMENTS 0030316 of 1897 United Kingdom ............... 220/669

*Primary Examiner*—Allan N. Shoap
*Assistant Examiner*—Niki M. Kopsidas
*Attorney, Agent, or Firm*—Louis J. Bachand

[57] ABSTRACT

A measuring vial for automatically determining correct number of fluid aliquots to be mixed with other materials such as dental alginate impression powders comprises a cylinder having an extended recess, an outlet port in the recess, the outlet port being at the height of the meniscus height of the desired quantity of fluid, any excess fluid being lost through the outlet port until the correct quantity is determined. A finger in the recess over the outlet blocks loss of fluid where desired.

17 Claims, 2 Drawing Sheets

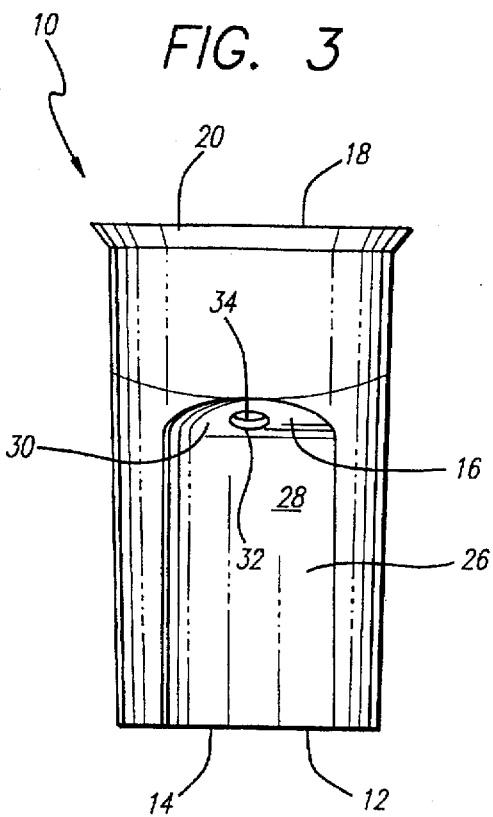
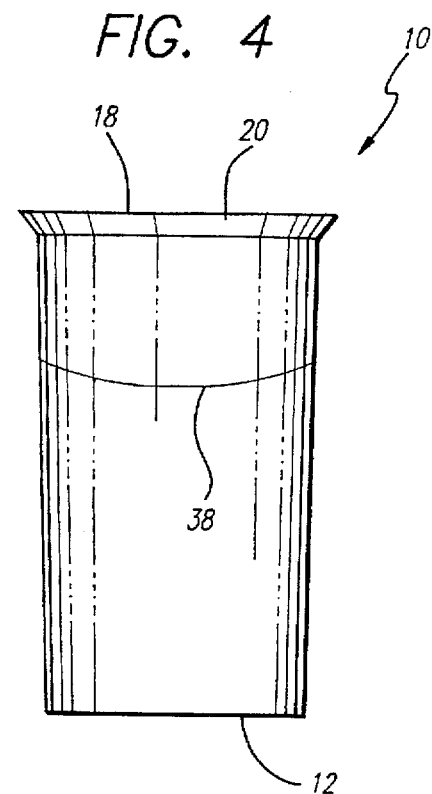
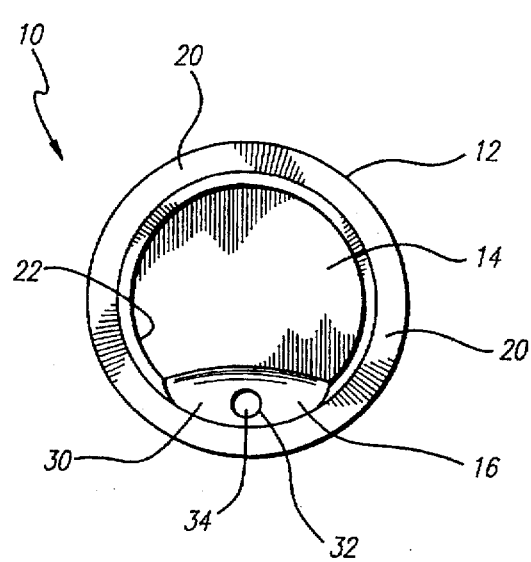
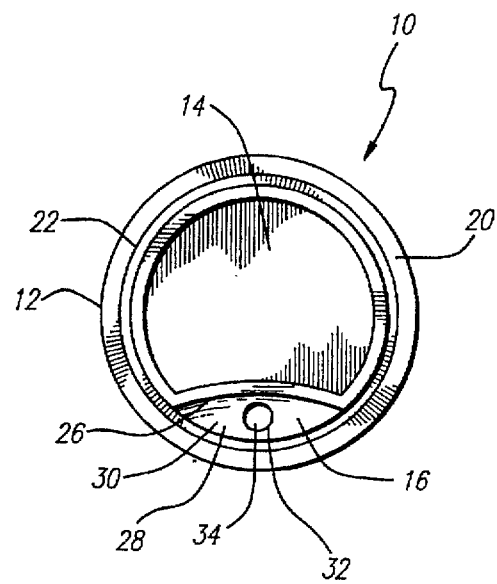

ALIQUOT PORTION MEASURING VIAL WITH OVERFILL CONTROL

TECHNICAL FIELD

This application relates to measuring vials suitable for the precise measurement of targeted quantities of fluids such as aliquot portions of water to be mixed with dental alginate impression powders, dental die stone powders and other materials needing accurate additions of a second, fluid material. More particularly, the invention relates to such vials having overfill control so that precise quantities of fluid can be obtained automatically during normal use of the vial, without overfilling, dumping, refilling and redumping in an over-under, nearly asymptotical process of approach to the targeted quantity of fluid.

BACKGROUND OF THE INVENTION

The present vial is especially, but not exclusively, useful in dental alginate and dental die stone preparations. Dental alginates and dental die stone need precisely measured amounts of water to properly and predictably react. Dental manufacturers design their products to blend a given aliquot of powder with a given aliquot of water, such as two scoops of powder to two aliquots of water for a frequently used amount of mixed material. Other amounts require less powder and less water, and vice versa for increased amounts of powder, but always in a fixed ratio of aliquots. It has been the case that in the absence of ease of rapid determination of portions, the dental office will use less than ideal ratios of powder and water. This can lead to imperfect results in impression taking, and dental die stone preparation.

SUMMARY OF THE INVENTION

It is an object of the present invention, therefore, to provide for the rapid and precise measurement of targeted numbers of aliquots of fluids such as water to be mixed with other materials such as reactive powders, or for myriad other purposes. It is another object to provide a measuring vial which is fill level self-limiting, with a predetermined targeted level of fill corresponding to a commonly used aliquot portion, e.g. two aliquots of water to be mixed with two scoops/aliquots of powder. It is yet another object to provide a measuring vial in which the generally cylindrical vial has a stepped base so that a portion of the base is elevated from the remainder, with a commensurate reshaping of the vial sidewall, to form an elongated, dished recess, at the upper end of which the upper portion of the vial base is located. The vial is provided with an outlet port at the upper base portion, the outlet port corresponding in placement to the height of the targeted number of aliquots frequently preferred to be measured in the vial, e.g. two aliquots.

The stepped base affords substantial savings in mold design and cycling time, as the vials can be molded in simple injection molds with no moving parts being needed to form recesses, outlet ports and other features of the vials of the invention.

The outlet port can be located at any desired level of vial contents, e.g. a single aliquot, or any other mount. It is a further object of the invention to have the outlet port be pierced through the recess wall in a manner to be knocked out if desired by the user, or not.

It is still another object to provide for spilling of the vial contents above the desired level by having the outlet port opposite the meniscus of the vial fluid and below the indicated measuring line, if any, the outlet port being located and sized to spill any water forming a higher meniscus than one opposite the port, as would occur with overfilling of the vial, for example.

These and other objects of the invention to become apparent hereinafter are realized in a measuring vial having a stepped base, an open mouth, and a finger-grippable sidewall therebetween providing an enclosed common volume for a plurality of vertically disposed fluid aliquot portions, the sidewall having a finger receiving recess, one or more sidewall outlet ports, e.g. including one outlet port opposite to or within the recess, the outlet port being at the uppermost level of a selected aliquot portion within the vial and arranged to spill higher levels of fluid from the vial in response to the presence of such higher levels of fluid, whereby the vial is readily filled directly to the level of the selected aliquot portion and not beyond even with excess mounts of fluid being added unless a finger within the recess blocks the outlet port.

In this and like embodiments, typically, the vial comprises synthetic organic plastic, the vial encloses two or three aliquot portions, the outlet port being placed at a level which limits contents of the vial to one or two aliquot portions, respectively, the vial has a longitudinal axis, the recess extending parallel to the vial longitudinal axis from the outlet to the vial base in base step defined relation, the recess is of substantially uniform cross section throughout its length below the outlet port to the base, the recess includes a sloped shoulder between the recess and the vial sidewall, the outlet port being formed in the recess sloped shoulder, and the vial has a longitudinal axis, the recess sloped shoulder extending at a downward and inward angle relative to the vial longitudinal axis, the outlet port extending through the recess sloped shoulder.

In a preferred embodiment, the invention provides a measuring vial having a stepped base, an open mouth, and a finger-grippable sidewall therebetween providing an enclosed common volume for a plurality of vertically disposed fluid aliquot portions, the sidewall having a finger receiving recess defined by the base step, a sidewall outlet port within the recess, the outlet port being at the uppermost level of a selected aliquot portion within the vial and arranged to spill higher levels of fluid from the vial in response to the presence of such higher levels of fluid, the fluid forming a meniscus within the vial, the outlet port being opposite the curved portion of the meniscus and sized to spill any increase in fluid raising the meniscus above the outlet port, whereby the vial is readily filled directly to the level of the selected aliquot portion and not beyond even with excess amounts of fluid being added unless a finger within the recess blocks the outlet port.

In this and like embodiments, the vial is divided along its length by at least one visible measurement indicium corresponding to the outer upper edge of the meniscus of a target level of fluid fill of the vial, the outlet port lying beneath the target level measurement indicium and opposite the curved portion of said meniscus, the fluid is water, and the outlet is from about 1/8 to about 1/4 inch in its largest transverse dimension, the vial comprises synthetic organic plastic, the vial outlet port has a maximum transverse dimension size to spill water from above the outlet port but not from the meniscus opposite the outlet port, the outlet being selectively finger closable, the vial has a longitudinal axis, the recess being extended longitudinally in parallel to the vial longitudinal axis from the outlet to the vial base, the recess defining a finger rest surrounding the outlet port, the recess is of substantially uniform cross section throughout its length below the outlet to the base, the recess includes a downwardly facing shoulder between the recess and the vial sidewall, the outlet port being formed in the recess shoulder, and the recess shoulder extends inwardly at a downward angle toward to the vial longitudinal axis, the outlet port extending through the recess shoulder at substantially a right angle to the shoulder.

In a particularly preferred embodiment, the invention provides a measuring vial having a generally circular base stepped to have a major, nearly circular, lower portion upon which the vial rests and a complementary minor, arcuate, upper portion, a generally circular open mouth, and a finger-grippable generally cylindrical sidewall therebetween providing an enclosed common volume for a plurality of vertically disposed fluid aliquot portions, the stepped base forming in the sidewall a longitudinally extended arcuate recess of substantially uniform cross section along substantially less than the full length of the sidewall, the recess transitioning to the sidewall along a sloped shoulder extending between the sidewall and the recess, the shoulder defining a finger rest, an outlet port pierced through the shoulder and arranged to be blocked by a finger on the finger rest, the outlet port being at the upper portion of the stepped base and at the uppermost level of a selected aliquot portion within the vial and arranged to spill higher levels of fluid from the vial in response to the presence of such higher levels of fluid, whereby the vial is readily filled directly to the level of the selected aliquot portion and not beyond even with excess amounts of fluid being added unless a finger on the finger rest blocks the outlet port.

The invention further contemplates the method of manufacturing an aliquot portion measuring vial having a bottom and a sidewall by injection molding, including forming a raised step in a minor portion of the vial bottom, the step extending a selected distance along and into the sidewall, and defining an outlet port in the raised step, the outlet port being at the height of a desired number of aliquot portions less than the capacity of the vial and sized for spilling from the vial any contents greater than the height of the outlet port.

BRIEF DESCRIPTION OF THE DRAWINGS

The invention will be further described in conjunction with the attached drawings in which:

FIG. 3 is a front elevation view thereof,

FIG. 4 is a rear elevation view thereof,

FIG. 5 is a top plan view thereof; and,

FIG. 6 is a bottom plan view thereof

DESCRIPTION OF THE PREFERRED EMBODIMENTS

Figure 1:
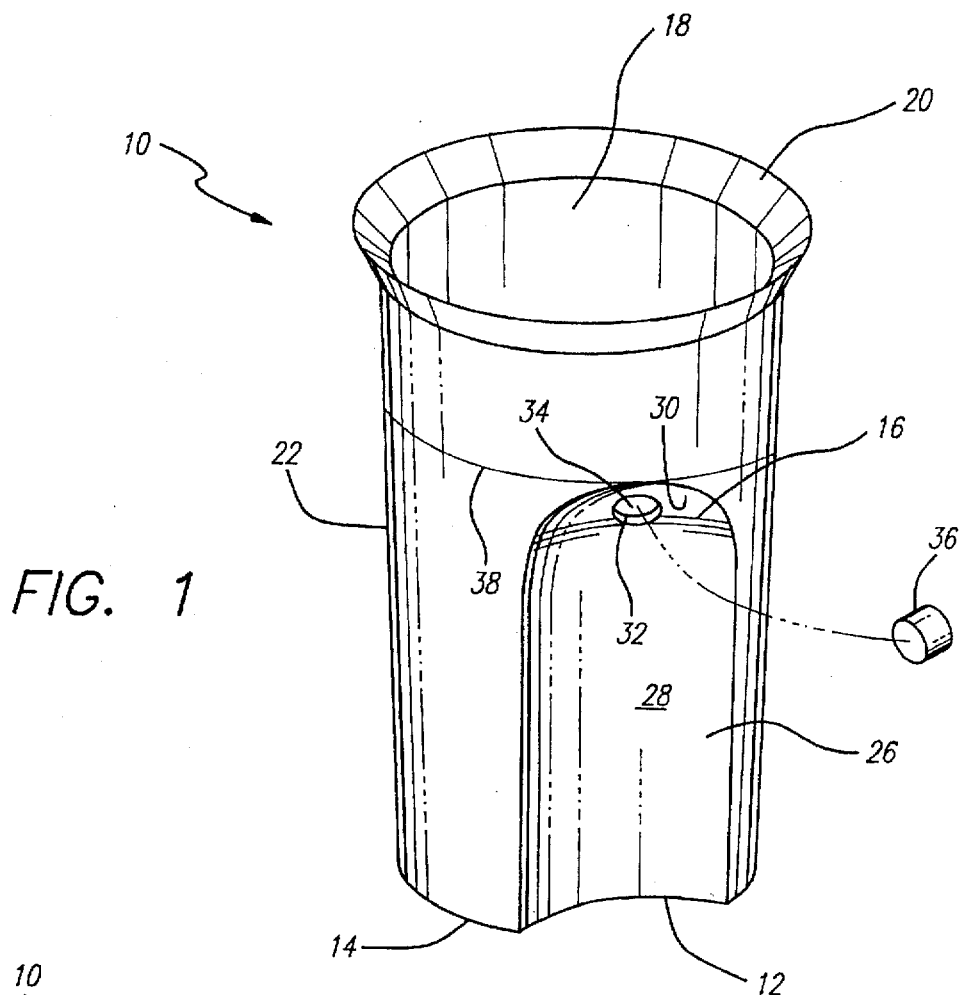
FIG. 1 is an axonometric view of the invention aliquot measuring vial.

The term aliquot herein refers to one or more of like sized fractional portions of a quantity of a fluid, e.g. a third of a whole is an aliquot, two-thirds of a whole is two aliquots, and so on. The present vial has a given capacity which can be thought of as divided into aliquot portions. In dental alginate preparation, for example, the dental assistant uses an aliquot of the alginate powder, conveniently measured in scoopfuls, and needs to use the proper corresponding aliquot of water. The vial is sized to provide the proper amounts of water, and suitably marked with indicia of the different aliquots, the first aliquot corresponding to one scoop of powder, the second aliquot two scoops and so on. Close correspondence of the liquid and powder aliquots is important to optimum performance from the mixed alginate impression material. In dental die stone preparation one or two aliquots of water are added to corresponding amounts of gypsum powder.

Precision of scoops is less a problem than precision of the fluid since the scoop is easily leveled with a spatula. The filling of the vial is usually a matter of trial and error as the desired target is approximated from above, then below, then above and so on. This difficulty is compounded by having to take one's eye off the vial to add water, lowering the vial to a tap, then bringing the vial to a position enabling checking of the level of filling. The invention provides a means of automatically preventing overfilling and in a manner that rapid filling with water at the tap can be used to fill without concern for overfilling or underfilling, as filling continues until there is spillage and at that point the vial is at the target level of filling.

With reference now to the drawings, in FIGS. 1–6 an illustrative embodiment of the invention measurement vial is shown at 10. The vial 10 has a stepped base 12 with a major, lower portion 14 and a complementary, minor, upper portion 16 spaced approximately two-thirds up the length of the vial. This height corresponds to a level of two aliquots of fluid below and a third aliquot of fluid above in this embodiment. The vial 10 has an open mouth 18 which is suitably flared as shown to form circular lip 20. Vial sidewall 22 extends between the base 12 and the mouth 18. Sidewall 22 is shown as a cylindrical wall of circular cross-section; the sidewall can have other cross-sections such as triangular, other polygonal, oval, or any other convenient shape which affords finger grippability, and of like or unlike uniformity in transverse dimension along its length.

In the embodiment shown, the vial 10 encloses a volume of fluid 24, water in the case of alginate impression material preparation, or any other powder or liquid fluid suited to be measured in the vial.

The sidewall 22 curves inwardly along one face 26 thereof to form a recess 28 extending parallel to and spaced from the longitudinal axis of the vial 10, of uniform cross section along its length, and commencing at the base upper portion 16 and extending down to the base lower portion 14. The displacement of the base minor, upper portion 16 from the remainder of the base forms the recess 28, the base portion forming a shoulder 30 defining the transition between the sidewall 22 and the recess. The base portion 16 can be planar and extend normal to the vial longitudinal axis like the base portion 14 but for purposes to be described below the illustrated configuration is preferred.

There is a substantial manufacturing advantage in having the base 12 be bifurcated so as to form the recess 28 as the vial 10 can be injection molded with the indicated shape, and the outlet port to be described, and nonetheless removed from the mold directly without costly resort to movable members in the mold halves to form the configuration and port. The indicated shape of the vial 10 can be slipped from a male mold cavity member with provision of only the normal draft used in design of molded parts.

The self-limiting-fill feature of the invention is achieved by the strategic placement of a hole 32 forming an outlet port 34 in the recess 28 at the top of the recess and through the shoulder 30. By design this height corresponds to the height of fluid amounting to a target number of aliquots of fluid in the form of outlet port 34. Additional holes can be used, e.g. opposite hole 32, or above or below; such added holes can be covered with fingers if not desired to be used.

The outlet port 34 comprises the hole 32 pierced through the shoulder 30. In some cases the hole 32 will be only partly formed by incompletely piercing the shoulder 30 leaving a fluid-tight web 36 of material in place to be knocked out (FIG. 1) or not depending on whether the outlet port 34 feature is to be used. Web 36 can be formed by mating mold members providing a reduced cross section locally in shoulder 30.

The location of the outlet port 34 is fixed to readily achieve the target quantum of fluid 24. A line 38 or other quantity indicium is suitable etched, painted or molded onto the vial sidewall 22. The line 38 is typical of the markings of the past in that it indicates where the top of the fluid is to be in order to achieve the target number of aliquots. As is known, fluids, particularly high surface tension liquids such as water, form a meniscus in a vial (FIG. 2), that is the fluid 24 forms a column 40 which has an upwardly concave surface 42 with a circular edge 44 higher than the main body 46 of the fluid column and clinging to the vial sidewall 22. It has been found that to achieve the precise height of fluid desired with the present invention, i.e. to obtain just the desired number of aliquots, the outlet port 34 is optimally to be located opposite the concave surface 42, assuming the fluid circular edge 44 is at the line 38, and sized to overcome the surface tension of the fluid. For example, for water as the fluid the outlet port 34 preferably has a maximum transverse dimension (diameter of the maximum cross section) of from about ⅛ inch to about ¼ inch. When so provided, the vial 10 will readily fill to the line 38 and only the line 38, as greater amounts of water, i.e. increased height in the column 40, increase the hydrostatic pressure on the top of the column, overcome the surface tension forces enabling the water to bridge the outlet port 34 without passing through the port. Thus, addition of water past the line 38 simply causes excess water to flow from the vial 10 until the nonflow equilibrium is restored and that is the point at which the edge 44 of the column 40 is at the line, for at that point water will not flow through the outlet port 34.

Figure 2:
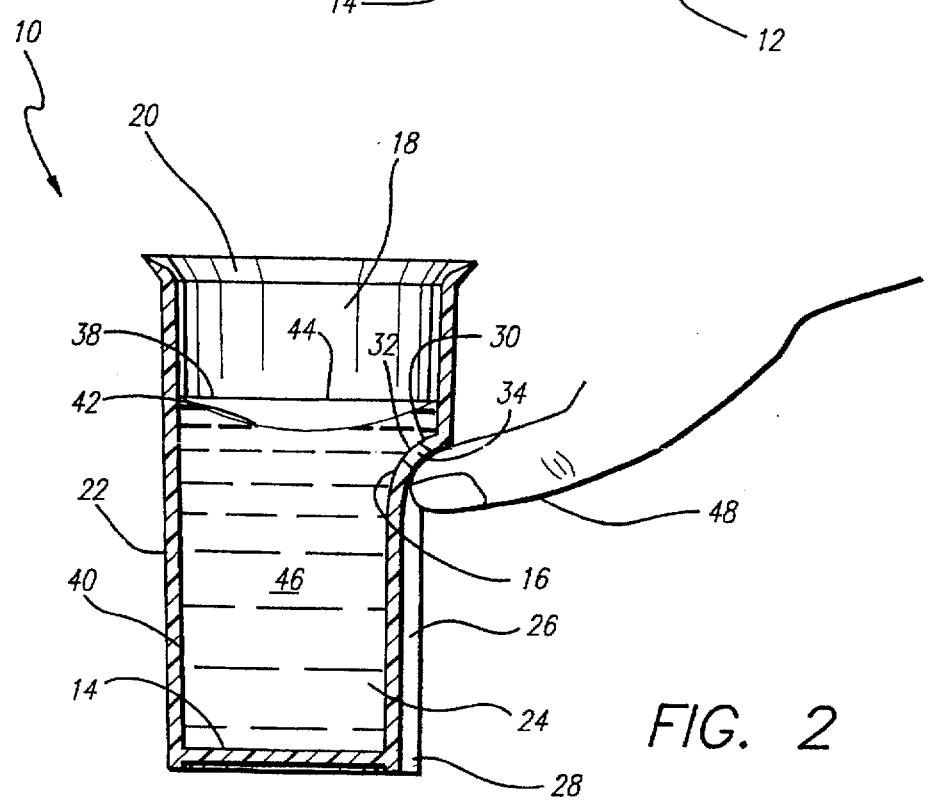
FIG. 2 is a view thereof in vertical section.

The illustrated vial 10 is arranged for use in obtaining readily two aliquots of water from a three aliquot size vial for mixing with two scoops of alginate powder. If it is desired to use three scoops of alginate powder and thus three aliquots of water will be needed, the vial 10 is readily adapted by putting a finger in the recess 28, at the shoulder 30, and blocking the outlet port 34 with the finger 48, as shown in FIG. 2. In a vial embodiment especially useful for dental die stone preparation, plural, vertically separated, outlet ports can be provided with the user closing the lower with a finger when fluid fill to the upper outlet port is desired.

The materials of construction of the vial 10 are not narrowly critical with metal, plastic, particularly synthetic organic plastic, or glass being suitable.

The invention thus provides for the rapid and precise measurement of targeted numbers of aliquots of fluids such as water to be mixed with other materials such as alginate powders, die stone gypsum, and the like, or for other purposes through a measuring vial which is fill level self-limiting, with a predetermined targeted level of fill corresponding to a commonly used aliquot portion, e.g. two aliquots of water to be mixed with two scoops/aliquots of powder. The vial has a stepped base so that a portion of the base is elevated from the remainder, with a commensurate reshaping of the vial sidewall, to form an elongated, dished recess, at the upper end of which the upper portion of the vial base is located. The vial is provided with an outlet port at the upper base portion, the outlet port corresponding in placement to the height of the targeted number of aliquots frequently preferred to be measured in the vial, e.g. two aliquots. The stepped base affords substantial savings in mold design and cycling time, as the vials can be molded in simple injection molds with no moving parts being needed to form recesses, outlet ports and other features of the vials of the invention. The outlet port can be located at any desired level of vial contents, e.g. a single aliquot, or any other amount with the outlet port opposite the meniscus of the vial fluid and below the indicated measuring line, if any, the outlet port being located and sized to spill any water forming a higher meniscus than one opposite the port, as would occur with overfilling of the vial.

The foregoing objects of the invention are thus met.

I claim:

1. Measuring vial having a base, an open mouth, and a finger-grippable sidewall therebetween providing an enclosed common volume for a plurality of vertically disposed fluid aliquot portions, said sidewall having a finger receiving recess extending from said base to a sloped shoulder above said base and below said vial mouth, a sidewall outlet port in said recess sloped shoulder, said outlet port being at the uppermost level of a selected aliquot portion within said vial and arranged to spill higher levels of fluid from said vial in response to the presence of such higher levels of fluid, whereby said vial is readily filled directly to the level of said selected aliquot portion and not beyond even with excess amounts of fluid being added unless a finger within said recess blocks said outlet port.

2. The measuring vial according to claim 1, in which said vial comprises plastic.

3. The measuring vial according to claim 1, in which said vial encloses two or three aliquot portions, said outlet port being placed at a level which limits contents of the vial to one or two aliquot portions, respectively.

4. The measuring vial according to claim 1, in which said vial has a longitudinal axis, said recess extending parallel to said vial longitudinal axis from said outlet to said vial base.

5. The measuring vial according to claim 4, in which said recess is of substantially uniform cross section throughout its length below said outlet to said base.

6. The measuring vial according to claim 1, in which said outlet port is downwardly directed.

7. The measuring vial according to claim 6, in which said vial has a longitudinal axis, said recess sloped shoulder extending at a downward and inward angle relative to said vial longitudinal axis, said outlet port extending through said recess sloped shoulder.

8. Measuring vial having a base, an open mouth, and a finger-grippable sidewall therebetween providing an enclosed common volume for a plurality of vertically disposed fluid aliquot portions, said sidewall having a finger receiving recess with a downardly facing shoulder, said shoulder defining an outlet port spaced from the plane of said base, said outlet port being at the uppermost level of a selected aliquot portion within said vial and arranged to spill higher levels of fluid from said vial in response to the presence of such higher levels of fluid, said fluid forming a meniscus within said vial, said outlet port being opposite the curved portion of said meniscus and sized to spill an increase in fluid raising said meniscus above said outlet port, whereby said vial is readily filled directly to the level of said selected aliquot portion and not beyond even with excess amounts of fluid being added unless a finger within said recess blocks said outlet port.

9. The measuring vial according to claim 8, in which said vial is divided along its length by at least one measurement indicium corresponding to the outer upper edge of the meniscus of a target level of fluid fill of said vial, said outlet port lying beneath said target level measurement indicium.

10. The measuring vial according to claim 8, in which said fluid is water, and said outlet is from about 1/8 to about 1/4 inch in its largest transverse dimension.

11. The measuring vial according to claim 8, in which said vial comprises synthetic organic plastic.

12. The measuring vial according to claim 11, in which said vial outlet port has a maximum transverse dimension size to spill water from above said outlet port but not from the meniscus opposite said outlet port, said outlet being selectively finger closable.

13. The measuring vial according to claim 12, in which said vial has a longitudinal axis, said recess being extended longitudinally in parallel to said vial longitudinal axis from said outlet to said vial base, said recess defining a finger rest surrounding said outlet port.

14. The measuring vial according to claim 13, in which said recess is of substantially uniform cross section throughout its length below said outlet to said base.

15. The measuring vial according to claim 14, in which said outlet port is downwardly directed.

16. The measuring vial according to claim 15, in which said recess shoulder extends inwardly at a downward angle toward to said vial longitudinal axis, said outlet port extending through said recess shoulder at substantially a right angle to said shoulder.

17. Measuring vial having a generally circular base comprising a major, nearly circular, lower portion upon which the vial rests and a complementary minor, arcuate, upper portion spaced from the plane of said base lower portion, a generally circular open mouth, and a finger-grippable generally cylindrical sidewall therebetween providing an enclosed common volume for a plurality of vertically disposed fluid aliquot portions, a longitudinally extended arcuate recess of substantially uniform cross section along substantially less than the full length of said sidewall, said recess transitioning to said sidewall along a sloped shoulder, said shoulder defining a finger rest, and outlet port pierced through said shoulder and arranged to be blocked by a finger on the finger rest, said outlet port being at said upper portion of said base and at the uppermost level of a selected aliquot portion within said vial and arranged to spill higher levels of fluid from said vial in response to the presence of such higher levels of fluid, whereby said vial is readily filled directly to the level of said selected aliquot portion and not beyond even with excess amounts of fluid being added unless a finger on said finger rest blocks said outlet port.

* * * * *